United States Patent
Woster et al.

(10) Patent No.: US 10,000,474 B2
(45) Date of Patent: Jun. 19, 2018

(54) HISTONE DEACETYLASE INHIBITORS AND USES THEREOF

(71) Applicant: MUSC FOUNDATION FOR RESEARCH DEVELOPMENT, Charleston, SC (US)

(72) Inventors: Patrick M. Woster, Charleston, SC (US); Youxuan Li, Greenbelt, MD (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days. days.

(21) Appl. No.: 15/526,040

(22) PCT Filed: Nov. 6, 2015

(86) PCT No.: PCT/US2015/059394
§ 371 (c)(1),
(2) Date: May 11, 2017

(87) PCT Pub. No.: WO2016/077163
PCT Pub. Date: May 19, 2016

(65) Prior Publication Data
US 2017/0313688 A1    Nov. 2, 2017

Related U.S. Application Data

(60) Provisional application No. 62/078,092, filed on Nov. 11, 2014.

(51) Int. Cl.
C07D 413/12 (2006.01)
C07D 263/34 (2006.01)
A61K 31/421 (2006.01)

(52) U.S. Cl.
CPC ......... C07D 413/12 (2013.01); C07D 263/34 (2013.01)

(58) Field of Classification Search
CPC combination set(s) only.
See application file for complete search history.

(56) References Cited

U.S. PATENT DOCUMENTS

2008/0090882 A1* 4/2008 Dorsch ............... C07D 233/68
                                                                514/365
2010/0298301 A1   11/2010 Reader et al.

FOREIGN PATENT DOCUMENTS

WO    2010055304 A2    5/2010
WO    2013174947 A1   11/2013

OTHER PUBLICATIONS

The International Search Report and Written Opinion, dated Feb. 23, 2016, in the related PCT Application No. PCT/US2015/059394.
Li et al., Discovery of a new class of histone deacetylase inhibitors with a novel zinc binding group. Medicinal Chemistry Communications 6: 613-618 and Supplemental Information, Dec. 16, 2014 [retrieved on Jan. 27, 2016]. Retrieved from the Internet: <URL: http://pubs.rsc.org/en/content/articlelanding/2015/md/c4md00401a#!divAbstract>. entire document.
PubChem, Substance Record for SID 134346683, Available Date: Feb. 15, 2012 [retrieved on Dec. 8, 2015]. Retrieved from the Internet.: <URL: https://pubchem.ncbi.nlm.nih .gov/substance/134346683/version/I#section=Top>. entire document.

* cited by examiner

*Primary Examiner* — Amanda L Aguirre

(57) ABSTRACT

Provided herein are compounds of the formula (I) as well as pharmaceutically acceptable salts thereof, wherein the substituents are as those disclosed in the specification. These compounds, and the pharmaceutical compositions containing them, are useful for the treatment of cancer. Additionally, provided is a method for treating cancer, comprising the step of administering a therapeutically effective amount of a compound according to formula (I), or a pharmaceutically acceptable salt thereof, and a pharmaceutically acceptable carrier to a patient in need thereof.

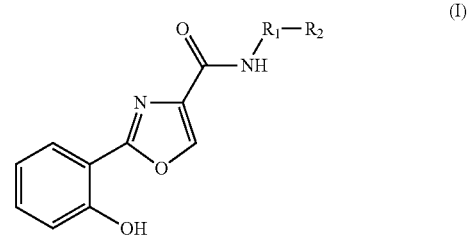

(I)

16 Claims, No Drawings

HISTONE DEACETYLASE INHIBITORS AND USES THEREOF

CROSS-REFERENCE TO RELATED APPLICATIONS

This application is a National Stage Application of PCT/US2015/059394 filed on Nov. 6, 2015, which claims priority from U.S. Provisional Patent Application No. 62/078,092 filed on Nov. 11, 2014. Each of prior mentioned applications is hereby expressly incorporated by reference herein in its entirety.

STATEMENT REGARDING FEDERALLY SPONSORED RESEARCH OR DEVELOPMENT

This invention was made with Government support under NIH/NCI grant 5RO1 CA149095. The Government has certain rights in the invention.

FIELD OF THE INVENTION

The invention is directed to compounds of formula (I):

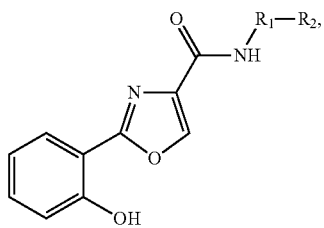

and to pharmaceutical compositions comprising the compounds. The compounds and compositions disclosed herein are histone deacetylase inhibitors useful for the treatment of cancer, such as, without limitation, leukemia and breast cancer.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Histone deacetylases (HDACs) are regarded as highly attractive targets for cancer drug discovery. Hyperacetylation induced by HDAC inhibitors leads to changes in gene expression and functional modifications of non-histone proteins, thereby triggering antitumor pathways. Well-characterized HDAC inhibitors typically contain three structural features useful for activity: an aromatic cap group, an aliphatic linker chain and a zinc binding group (ZBG). Based on molecular modeling studies involving the histone deacetylase-like protein (HDLP), these molecules appear to bind in a pocket in the HDAC active site that includes a channel region flanked by a zinc ion on one end, and a region that binds the cap group on the other end. In this model, the aromatic group and aliphatic chain of the inhibitor are buried in the enzyme pocket in such a way that the metal binding moiety coordinates the catalytic zinc ion. Structural studies to identify novel HDAC inhibitors has focused primarily on modifications to the aliphatic linker or the aromatic cap group, while less attention has been paid to the metal binding group, which is typically either a hydroxamic acid or a benzamide. However, hydroxamates suffer from low bioavailability and significant off-target effects that limit their clinical use. Similarly, benzamides contain an aniline moiety that may generate toxic metabolites in vivo.

There is a need, therefore, for the development of new HDAC inhibitors with ZBGs that possess minimal toxicity and improved pharmacokinetic profiles.

SUMMARY OF THE INVENTION

The present invention is directed to compounds according to formula (I):

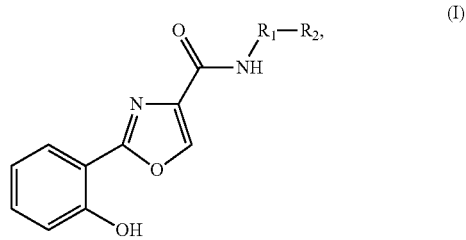

wherein:
$R_1$ is a bond, lower alkyl or phenyl; and
$R_2$ is -phenyl, optionally substituted independently with
—C(O)NH-phenyl, —C(O)OCH$_3$,
—C(O)OH or phenyl,
—CH(phenyl)$_2$,
-naphthalenyl,
-1H-indolyl,
-dioxoisoindolinyl,
—NHC(O)CH(phenyl)$_2$,
—NHC(S)NHCH2CH2CH(phenyl)$_2$,
—NHCH2CH2CH(phenyl)$_2$ or
—C(O)NH-phenyl,
or a pharmaceutically acceptable salt thereof.

The present invention is also directed to pharmaceutical compositions containing the compounds of formula (I) and to methods of using these compounds.

DETAILED DESCRIPTION OF THE INVENTION

Provided herein are potent HDAC inhibitors having a 2-(oxazole-2-yl)phenol ZBG. A feature of the invention is an o-hydroxyphenyl group that is directly connected to an oxazole aromatic ring to produce a cation binding site. Advantageously, the compounds of the invention are free of aniline moieties that can potentially generate toxic metabolites in vivo.

It is to be understood that the terminology employed herein is for the purpose of describing particular embodiments, and is not intended to be limiting. Further, although any methods, devices and materials similar or equivalent to those described herein can be used in the practice or testing of the invention, certain embodiments of such methods, devices and materials are now described.

As used herein, the term "alkyl", alone or in combination with other groups, refers to a branched or straight-chain monovalent saturated aliphatic hydrocarbon radical of one to twenty carbon atoms, in one embodiment one to sixteen carbon atoms, in another embodiment one to ten carbon atoms.

The term "lower alkyl", alone or in combination with other groups, refers to a branched or straight-chain alkyl radical of one to nine carbon atoms, in one embodiment one to six carbon atoms, in another embodiment one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, in one embodiment, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyli, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. In certain embodiments, fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In one embodiment of the invention, provided is a compound of formula (I):

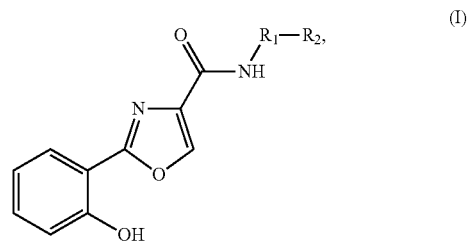

(I)

wherein:
$R_1$ is a bond or lower alkyl; and
$R_2$ is -phenyl, optionally substituted independently with
—C(O)NH-phenyl, —C(O)OCH$_3$, phenyl or —C(O)OH,
—CH(phenyl)$_2$,
-naphthalenyl,
-1H-indolyl,
-dioxoisoindolinyl,
—NHC(O)CH(phenyl)$_2$,
—NHC(S)NHCH$_2$CH$_2$CH(phenyl)$_2$,
—NHCH$_2$CH$_2$CH(phenyl)$_2$ or
—C(O)NH-phenyl,
or a pharmaceutically acceptable salt thereof.

In another embodiment of the present invention, provided is a compound of formula (I), wherein $R_1$ is a bond.

In another embodiment of the present invention, provided is a compound of formula (I), wherein $R_1$ is lower alkyl.

In another embodiment of the present invention, provided is a compound of formula (I), wherein $R_2$ is phenyl.

In another embodiment of the present invention, provided is a compound of formula (I), wherein $R_2$ is phenyl substituted independently with —C(O)NH-phenyl, —C(O)OCH$_3$, —C(O)OH or phenyl.

In another embodiment of the present invention, provided is a compound of formula (I), wherein $R_2$ is —CH(phenyl)$_2$.

In another embodiment of the present invention, provided is a compound of formula (I), wherein $R_2$ is naphthalenyl, 1H-indolyl or dioxoisoindolinyl.

In another embodiment of the present invention, provided is a compound of formula (I), wherein $R_2$ is —NHC(O)CH(phenyl)$_2$, —NHC(S)NHCH$_2$CH$_2$CH(phenyl)$_2$, —NHCH$_2$CH$_2$CH(phenyl)$_2$ or —C(O)NH-phenyl.

In another embodiment of the present invention, provided is a compound of formula (I), wherein $R_1$ is a bond and $R_2$ is phenyl, optionally substituted independently with —C(O)NH-phenyl, —C(O)OCH$_3$, —C(O)OH or phenyl.

In another embodiment of the present invention, provided is a compound of formula (I), wherein $R_1$ is a bond and $R_2$ is —CH(phenyl)$_2$.

In another embodiment of the present invention, provided is a compound of formula (I), wherein $R_1$ is lower alkyl and $R_2$ is —CH(phenyl)$_2$, -naphthalenyl, -1H-indolyl, -dioxoisoindolinyl, —NHC(O)CH(phenyl)$_2$, —NHC(S)NHCH$_2$CH$_2$CH(phenyl)$_2$, —NHCH$_2$CH$_2$CH(phenyl)$_2$ or —C(O)NH-phenyl.

In another embodiment of the present invention, provided is a compound of formula (I), wherein said lower alkyl is methyl, ethyl, propyl or butyl.

In another embodiment of the present invention, provided is a compound of formula (I), wherein said lower alkyl is methyl or ethyl.

In another embodiment of the present invention, provided is a compound of formula (I), wherein said lower alkyl is methyl.

In another embodiment of the present invention, provided is a compound of formula (I), wherein the compound is:
2-(2-Hydroxyphenyl)-N-phenyloxazole-4-carboxamide;
N-Benzhydryl-2-(2-hydroxyphenyl)oxazole-4-carboxamide;
N-(2,2-Diphenylethyl)-2-(2-hydroxyphenyl)oxazole-4-carboxamide;
N-(3,3-Diphenylpropyl)-2-(2-hydroxyphenyl)oxazole-4-carboxamide;
N-([1,1'-Biphenyl]-4-yl)-2-(2-hydroxyphenyl)oxazole-4-carboxamide;
N-([1,1'-Biphenyl]-4-ylmethyl)-2-(2-hydroxyphenyl)oxazole-4-carboxamide;
2-(2-Hydroxyphenyl)-N-(naphthalen-1-ylmethyl)oxazole-4-carboxamide;
N-(2-(1H-Indol-3-yl)ethyl)-2-(2-hydroxyphenyl)oxazole-4-carboxamide;
N-(4-(1,3-Dioxoisoindolin-2-yl)butyl)-2-(2-hydroxyphenyl)oxazole-4-carboxamide;
N-(4-(2,2-Diphenylacetamido)butyl)-2-(2-hydroxyphenyl)oxazole-4-carboxamide;
N-(4-(3-(3,3-Diphenylpropyl)thioureido)butyl)-2-(2-hydroxyphenyl)oxazole-4-carboxamide;
N-(4-((3,3-Diphenylpropyl)amino)butyl)-2-(2-hydroxyphenyl)oxazole-4-carboxamide hydrochloride;
Methyl 4-((2-(2-hydroxyphenyl)oxazole-4-carboxamido)methyl)benzoate;
4-((2-(2-Hydroxyphenyl)oxazole-4-carboxamido)methyl)benzoic acid;
2-(2-Hydroxyphenyl)-N-(4-(phenylcarbamoyl)benzyl)oxazole-4-carboxamide; or
2-(2-Hydroxyphenyl)-N-(2-oxo-2-(phenylamino)ethyl)oxazole-4-carboxamide.

In a further embodiment of the present invention, provided is a pharmaceutical composition, comprising a therapeutically effective amount of a compound of formula (I) or a pharmaceutically acceptable salt thereof and a pharmaceutically acceptable carrier.

In a yet further embodiment of the present invention, provided is a method for treating cancer, comprising the step of administering a therapeutically effective amount of a compound according to formula (I), or a pharmaceutically acceptable salt thereof, and a pharmaceutically acceptable carrier to a patient in need thereof.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Certain embodiments, water, saline, aqueous dextrose, and glycols are liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. In one embodiment, the therapeutically effective amount is in an amount of from about 1 mg to about 500 mg per day. In another embodiment, one to four doses can be given per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. For example, the compounds of formula I can be prepared according to the following scheme:

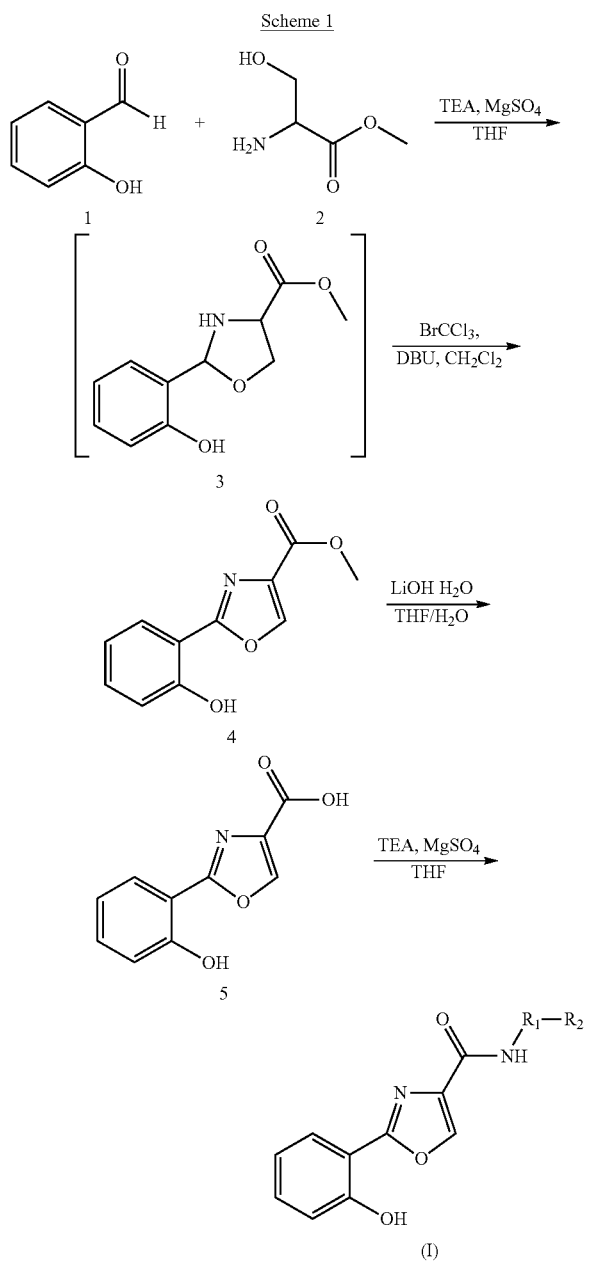

As shown in Scheme 1, the condensation of salicylaldehyde 1 with L-serine methyl ester hydrochloride 2 yields the intermediate 1,3-oxazolidine 3, which can then be oxidized in situ in the presence of BrCCl$_3$/DBU to afford the corresponding 1,3-oxazole methyl ester 4. The methyl ester 4 can then be cleaved in the presence of lithium hydroxide to form the corresponding carboxylate 5, which can then be coupled to the appropriate amines to afford the compounds of formula (I).

The invention will now be further described in the Examples below, which are intended as an illustration only and do not limit the scope of the invention.

EXAMPLES

All reagents were purchased from Acros Organics, Alfa Aesar, Fisher Scientific, Matrix Scientific, Oakwood Products, Sigma-Aldrich, TCI America, VWR International and were used without further purification except as noted below. Solvents tetrahydrofuran (THF), dichloromethane (DCM), methanol, dimethylformamide (DMF), acetonitrile and ethyl acetate were purified through SG Water® Glass Contour 6-position solvent purification system. Moisture-sensitive reactions were performed under argon with dried glassware and dry solvent. Preparative scale chromatographic procedures were carried out using TELEDYNE ISCO Combiflash® Rf with normal phase disposable columns RediSep® Rf (Gold/Universal, 4 g, 12 g, 24 g or 40 g). Thin-layer chromatography was conducted on TCL Silica gel 60 F254. Microwave reactions were carried out by using Biotage Initiator 2.5. Solvents were removed by rotary evaporation (Büchi Rotavapor R-114 and Büchi Water Bath B-490) and a vacuum pump (Heidolph Rotavac Valve Control). All $^1$H and $^{13}$C NMR spectra were recorded in CDCl$_3$, CD$_3$OD, or DMSO-d$_6$ using a Varian Mercury 400 MHz FT-NMR or a Varian UNITY INOVA 400 MHz FT-NMR and all chemical shifts were reported as δ values referenced to TMS. Mass spectrometric analysis was performed at a Waters Mass-Directed Autopurification system (LC/MS) using a 3100 single quadrupole Mass Detector. HPLC analysis was performed through a Waters ACQUITY H-Series UPLC with an ACQUITY UPLC® BEH C18 1.7 μm 2.1× 500 mm column using a gradient of 95% to 5% Buffer A over 10 min (Buffer A=water with 0.1% TFA; Buffer B=HPLC grade acetonitrile) at 0.5 mL/min at room temperature.

I. Preparation of Representative Intermediates of the Invention

Methyl 2-(2-hydroxyphenyl)oxazole-4-carboxylate (4)

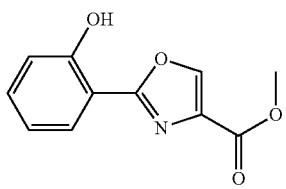 [SMILES: COC(=O)c1coc(-c2ccccc2O)n1]

Step A: A 25 ml round bottom single-neck flask was charged with L-serine methyl ester hydrochloride 5 (0.156 g, 1 mmol), magnesium sulfate (0.121 g, 1 mmol) and tetrahydrofuran (5 ml). The mixture was treated with salicylaldehyde 4 (0.122 g, 1 mmol) and triethylamine (0.202 g, 2 mmol). The resulting mixture was stirred at room temperature for 12 hours and filtered through a 0.45 μM PTFE syringe filter. The combined filtrate containing 6 was concentrated to dryness and used for the next step without further purification.

Step B: The crude oxazolidine 6 from step A was dissolved in 5 ml DCM, and the solution was cooled to 0° C. and treated with bromotrichloromethane (0.298 ml, 3 mmol) and 1,8-diazabicyclo[5.4.0]undec-7-ene (0.453 ml, 3 mmol). The resulting mixture was stirred at 0° C. for 2 hours and then at room temperature for another 10 hours. The reaction mixture was poured directly onto a 40 g normal phase disposable RediSep® Rf column. The product was eluted (0-40% ethyl acetate/hexane) to afford the title compound 4 (0.053 g, 23%) as a white, amorphous solid. $^1$H NMR (δ, ppm, CDCl$_3$): 3.97 (s, 3H), 7.00 (t, 1H), 7.12 (d, 1H), 7.43 (t, 1H), 7.86 (dd, 1H), 8.28 (s, 1H), 10.68 (s, 1H). UPLC: 5.458 min. ESI-MS m/z: calculated: 220.058; found: 220.223 [M+H]$^+$.

2-(2-Hydroxyphenyl)oxazole-4-carboxylic acid (5)

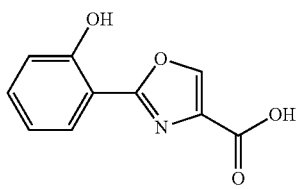 [SMILES: O=C(O)c1coc(-c2ccccc2O)n1]

A 5 ml aqueous solution of lithium hydroxide monohydrate (0.04 g, 1 mmol) was added dropwise over a period of 15 min to a 10 ml THF solution of compound 4 (0.03 g, 0.14 mmol) at 0° C. The reaction mixture was slowly warmed up to room temperature and stirred overnight. Then the whole mixture was again cooled to 0° C. and acidified by adding 1 M dilute HCl solution to PH=3. Later the whole mixture was extracted with three 50 ml portions of ethyl acetate. The combined organic layers were washed with brine and dried over anhydrous magnesium sulfate and filtered. The solvent was then concentrated to yield the product 5 as a white amorphous solid (0.025 g, 88%). $^1$H NMR (δ, ppm, CD$_3$OD): 7.00 (t, 1H), 7.05 (d, 1H), 7.44 (t, 1H), 7.90 (t, 1H), 8.61 (s, 1H). UPLC: 4.572 min. ESI-MS m/z: calculated: 206.048; found: 206.147 [M+H]$^+$.

II. Preparation of Representative Embodiments of the Invention

Example 1

2-(2-Hydroxyphenyl)-N-phenyloxazole-4-carboxamide

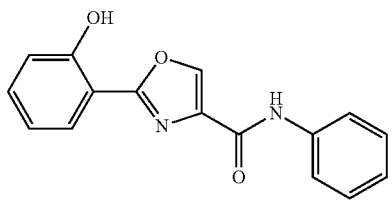 [SMILES: O=C(Nc1ccccc1)c1coc(-c2ccccc2O)n1]

Compound 5 (0.015 g, 0.07 mmol) was dissolved in 3 ml DCM in a 5 ml microwave reaction tube and aniline (0.007 g, 0.08 mmol) was added into above solution followed by HATU (0.038 g, 0.1 mmol) and DIPEA (0.013 g, 0.1 mmol). Microwave reaction was carried out in Biotage Initiator 2.5 for 25 min at 80° C. The reaction mixture was extracted with water and DCM and organic layer was later washed by 0.1 M dilute HCl solution, saturated sodium bicarbonate solution and brine consecutively. Then the organic layer was dried over anhydrous magnesium sulfate, filtered and concentrated to give crude product. Purification by Combiflash (20%-100% ethyl acetate/hexane) afforded a pure product as a white amorphous solid (0.025 g, 88%). $^1$H NMR (δ, ppm, CDCl$_3$): 7.04 (td, 1H), 7.14 (d, 1H), 7.21 (t, 1H), 7.42 (t, 2H), 7.47 (td, 1H), 7.71 (d, 2H), 7.91 (dd, 1H), 8.38 (s, 1H), 8.41 (brs, 1H). $^{13}$C NMR (δ, ppm, CDCl$_3$): 110.27, 117.42, 120.16, 120.25, 125.04, 126.72, 129.20, 133.55, 136.09, 136.92, 140.86, 156.90, 157.55, 162.32. UPLC: 6.211 min.; m.p. 173-174° C.; ESI-MS m/z calculated: 281.0957; found: 281.232 [M+H]$^+$.

Example 2

N-Benzhydryl-2-(2-hydroxyphenyl)oxazole-4-carboxamide

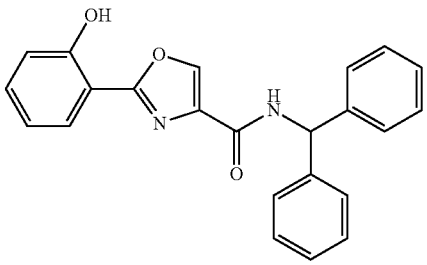 [SMILES: O=C(NC(c1ccccc1)c1ccccc1)c1coc(-c2ccccc2O)n1]

The compound of Example 2 was made from compound 5 (0.04 g, 0.22 mmol), benzhydrylamine (0.046 g, 0.25 mmol), HATU (0.114 g, 0.3 mmol) and DIPEA (0.039 g, 0.3 mmol) in 4 ml DCM using the procedure described for the synthesis of Example 1 in 95% yield as an off-white amorphous solid (0.07 g). $^1$H NMR (δ, ppm, CDCl$_3$): 6.49 (d, 1H), 7.02 (t, 1H), 7.09 (d, 1H), 7.37-7.47 (m, 9H), 7.45 (t, 1H), 7.89 (dd, 1H), 8.29 (s, 1H), 10.24 (brs, 1H). $^{13}$C NMR (δ, ppm, CDCl$_3$): 56.71, 110.33, 117.32, 120.08, 126.63, 127.51, 127.76, 128.85, 133.40, 135.64, 140.59, 140.90, 156.83, 158.90, 161.30. UPLC: 7.032 min.; m.p. 226-227° C.; ESI-MS m/z calculated: 371.140; found: 371.274 [M+H]$^+$.

Example 3

N-(2,2-Diphenylethyl)-2-(2-hydroxyphenyl)oxazole-4-carboxamide

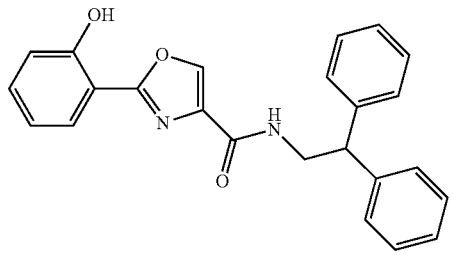 [SMILES: O=C(NCC(c1ccccc1)c1ccccc1)c1coc(-c2ccccc2O)n1]

The compound of Example 3 was made from compound 5 (0.05 g, 0.25 mmol), 2,2-diphenylethylamine (0.04 g, 0.2 mmol), HATU (0.114 g, 0.3 mmol) and DIPEA (0.039 g, 0.3 mmol) in 4 ml DCM using the procedure described in Example 1 in 86% yield as a white amorphous solid (0.066 g). $^1$H NMR (δ, ppm, CDCl$_3$): 4.13 (q, 2H), 4.34 (t, 1H), 6.73 (brs, 1H), 6.99 (t, 1H), 7.08 (d, 1H), 7.26-7.44 (m, 11H), 7.83 (d, 1H), 8.23 (s, 1H), 9.88 (brs, 1H). $^{13}$C NMR (δ, ppm, CDCl$_3$): 43.44, 50.45, 110.24, 117.36, 119.95, 126.57, 127.11, 128.05, 128.90, 133.34, 133.36, 135.53, 135.57, 140.03, 140.06, 141.54, 156.92, 159.66, 161.12. UPLC: 7.053 min.; m.p. 206-208° C.; ESI-MS m/z calculated: 385.155; found: 385.294 [M+H]$^+$.

Example 4

N-(3,3-Diphenylpropyl)-2-(2-hydroxyphenyl)oxazole-4-carboxamide

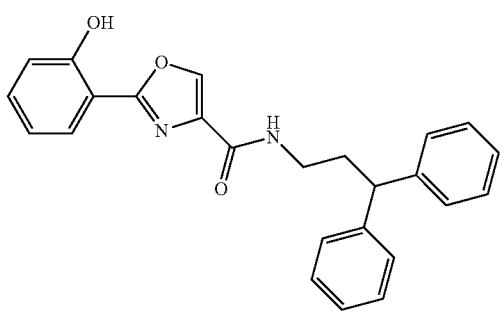 [SMILES: O=C(NCCC(c1ccccc1)c1ccccc1)c1coc(-c2ccccc2O)n1]

The compound of Example 4 was made from compound 5 (0.026 g, 0.127 mmol), 3,3-diphenylpropylamine (0.032 g, 0.15 mmol), HATU (0.076 g, 0.2 mmol) and DIPEA (0.032 g, 0.25 mmol) in 4 ml DCM using the procedure described in Example 1 in 70% yield as a pale tan amorphous solid (0.035 g). $^1$H NMR (δ, ppm, CDCl$_3$): 2.45 (q, 2H), 3.48 (q, 2H), 4.05 (t, 1H), 6.72 (t, 1H), 7.03 (t, 1H), 7.12 (d, 1H), 7.18-7.23 (m, 2H), 7.28-7.34 (m, 8H), 7.47 (td, 1H), 7.88 (dd, 1H), 8.24 (s, 1H), 10.18 (brs, 1H). $^{13}$C NMR (δ, ppm, CDCl$_3$): 35.13, 38.32, 49.26, 110.37, 117.36, 120.00, 126.53, 126.60, 127.74, 128.70, 133.31, 135.83, 139.99, 144.06, 156.92, 159.67, 161.13. UPLC: 7.321 min. ESI-MS m/z calculated: 399.171; found: 399.353 [M+H]$^+$.

Example 5

N-([1,1'-Biphenyl]-4-yl)-2-(2-hydroxyphenyl)oxazole-4-carboxamide

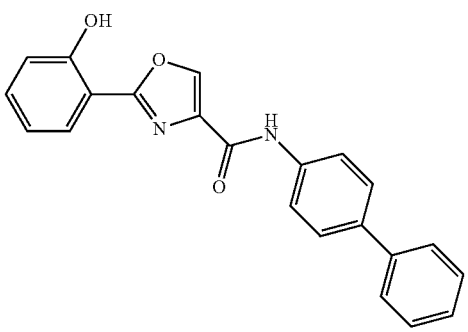 [SMILES: O=C(Nc1ccc(-c2ccccc2)cc1)c1coc(-c2ccccc2O)n1]

The compound of this Example was made from compound 5 (0.028 g, 0.13 mmol), 4-biphenylylamine (0.025 g, 0.15 mmol), HATU (0.068 g, 0.18 mmol) and DIPEA (0.026 g, 0.2 mmol) in 4 ml DCM using the procedure described in Example 1 in 84% yield as a white amorphous solid (0.039 g). $^1$H NMR (δ, ppm, CDCl$_3$): 7.05 (t, 1H), 7.15 (d, 1H), 7.37 (t, 1H), 7.37-7.40 (m, 3H), 7.45-7.50 (m, 4H), 7.65 (d, 2H), 7.92 (d, 1H), 8.39 (s, 1H), 8.49 (s, 1H), 10.20 (brs, 1H). $^{13}$C NMR (δ, ppm, CDCl$_3$): 110.27, 117.44, 120.17, 120.54, 126.74, 126.90, 127.28, 127.78, 128.84, 133.57, 136.07, 136.21, 137.88, 140.35, 140.90, 156.91, 157.55, 161.35. UPLC: 7.408 min.; m.p. 218-219° C.; ESI-MS m/z calculated: 357.124; found: 357.220 [M+H]$^+$.

Example 6

N-([1,1'-Biphenyl]-4-ylmethyl)-2-(2-hydroxyphenyl)oxazole-4-carboxamide

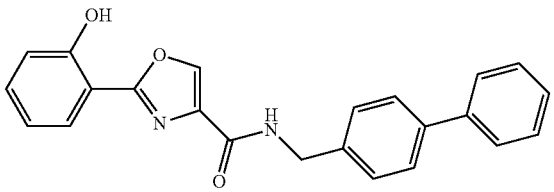 [SMILES: O=C(NCc1ccc(-c2ccccc2)cc1)c1coc(-c2ccccc2O)n1]

The compound of this Example was made from compound 5 (0.022 g, 0.1 mmol), 4-phenylbenzylamine (0.018 g, 0.1 mmol), HATU (0.057 g, 0.15 mmol) and DIPEA (0.02 g, 0.15 mmol) in 4 ml DCM using the procedure described in Example 1 in 65% yield as a white amorphous solid (0.024 g). $^1$H NMR (δ, ppm, CDCl$_3$): 4.73 (d, 2H), 7.02 (td, 1H), 7.08 (d, 1H), 7.12 (t, 1H), 7.36 (t, 1H), 7.39-7.48 (m, 5H), 7.60-7.62 (m, 4H), 7.89 (dd, 1H), 8.32 (s, 1H), 10.21 (brs, 1H). $^{13}$C NMR (δ, ppm, CDCl$_3$): 42.98, 110.32, 117.36, 120.03, 126.60, 127.13, 127.40, 127.61, 128.38, 128.81, 133.37, 135.71, 136.65, 140.36, 140.70, 140.82, 156.90, 159.70, 161.30. UPLC: 7.132 min.; m.p. 220-221° C.; ESI-MS m/z calculated: 371.1402; found: 371.343 [M+H]$^+$.

Example 7

2-(2-Hydroxyphenyl)-N-(naphthalen-1-ylmethyl)oxazole-4-carboxamide

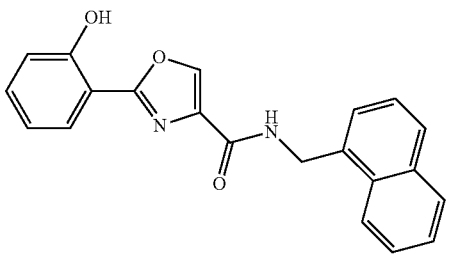 [SMILES: O=C(NCc1cccc2ccccc12)c1coc(-c2ccccc2O)n1]

The compound of Example 7 was made from compound 5 (0.022 g, 0.1 mmol), 1-naphthalenemethylamine (0.016 g, 0.1 mmol), HATU (0.057 g, 0.15 mmol) and DIPEA (0.02 g, 0.15 mmol) in 4 ml DCM using the procedure described in Example 1 in 81% yield as a white amorphous solid (0.028 g). $^1$H NMR (δ, ppm, CDCl$_3$): 5.11 (d, 2H), 6.99 (td, 1H), 7.02 (d, 1H), 7.12 (t, 1H), 7.40 (td, 1H), 7.47 (d, 1H), 7.51-7.60 (m, 3H), 7.82-7.87 (m, 2H), 7.90 (d, 1H), 8.10 (d, 1H), 8.30 (s, 1H), 10.19 (s, 1H). $^{13}$C NMR (δ, ppm, CDCl$_3$): 41.33, 110.29, 117.30, 119.96, 123.32, 125.41, 126.07, 126.56, 126.78, 128.87, 131.38, 132.83, 133.28, 133.92, 135.64, 140.37, 156.80, 159.48, 161.17. UPLC: 6.705 min. ESI-MS m/z calculated: 345.124; found: 345.262 [M+H]$^+$.

Example 8

N-(2-(1H-Indol-3-yl)ethyl)-2-(2-hydroxyphenyl)oxazole-4-carboxamide

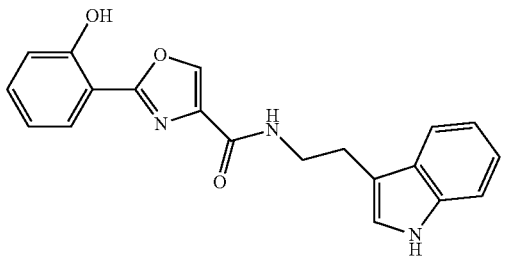 [SMILES: O=C(NCCc1c[nH]c2ccccc12)c1coc(-c2ccccc2O)n1]

The compound of Example 8 was made from compound 5 (0.022 g, 0.1 mmol), 2-(3-indolyl)ethylamine (0.021 g, 0.12 mmol), HATU (0.057 g, 0.15 mmol) and DIPEA (0.026 g, 0.2 mmol) in 4 ml DCM using the procedure described in Example 1 in 72% yield as a pale yellow amorphous solid (0.025 g). $^1$H NMR (δ, ppm, CDCl$_3$): 3.14 (t, 2H), 3.81 (q, 2H), 6.89 (brs, 1H), 7.02 (t, 1H), 7.10 (d, 1H), 7.15-7.20 (m, 2H), 7.25 (t, 1H), 7.42-7.46 (m, 2H), 7.69 (d, 1H), 7.87 (d, 1H), 8.23 (brs, 1H), 8.27 (s, 1H). $^{13}$C NMR (δ, ppm, CDCl$_3$): 25.35, 39.13, 110.35, 111.40, 112.63, 117.30, 118.69, 119.66, 120.00, 122.17, 122.41, 126.58, 127.01, 133.29, 135.87, 136.57, 139.94, 156.87, 159.60, 161.10. UPLC: 6.141 min. ESI-MS m/z calculated: 348.135; found: 348.316 [M+H]$^+$.

Example 9

N-(4-(1,3-Dioxoisoindolin-2-yl)butyl)-2-(2-hydroxyphenyl)oxazole-4-carboxamide

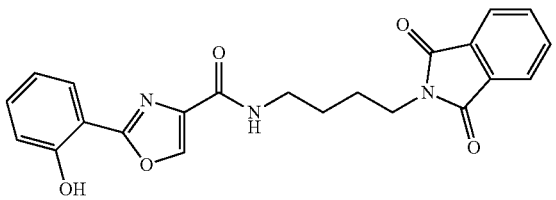 [SMILES: O=C(NCCCCN1C(=O)c2ccccc2C1=O)c1coc(-c2ccccc2O)n1]

The compound of this Example was made from compound 5 (0.04 g, 0.2 mmol), N-[4-(amino)butyl]phthalimide hydrochloride (0.056 g, 0.22 mmol), HATU (0.141 g, 0.3 mmol) and DIPEA (0.06 g, 0.5 mmol) in 4 ml DCM using the procedure described in Example 1 in 98% yield as a pale yellow amorphous solid (0.08 g). $^1$H NMR (δ, ppm, CDCl$_3$): 1.72 (quint, 2H), 1.83 (quint, 2H), 3.56 (q, 2H), 3.78 (t, 2H), 7.00 (td, 1H), 7.09 (d, 1H), 7.14 (t, 1H), 7.42 (td, 1H), 7.71-7.75 (m, 2H), 7.85-7.90 (m, 3H), 8.26 (s, 1H), 10.25 (s, 1H). $^{13}$C NMR (δ, ppm, CDCl$_3$): 26.11, 26.54, 37.24, 38.66, 110.42, 117.35, 119.93, 123.35, 126.59, 132.07, 133.22, 133.99, 135.89, 140.11, 156.90, 159.88, 161.13, 168.57. UPLC: 6.054 min. ESI-MS m/z calculated: 406.141; found: 406.295 [M+H]$^+$.

Example 10

N-(4-(2,2-Diphenylacetamido)butyl)-2-(2-hydroxyphenyl)oxazole-4-carboxamide

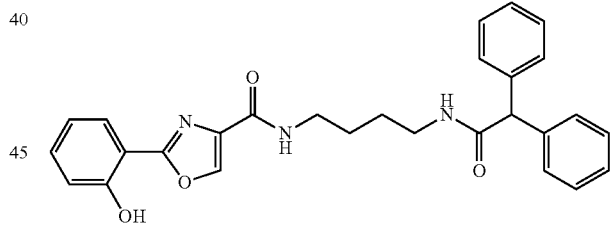

Compound 5 (0.021 g, 0.1 mmol) was dissolved in 10 ml DCM and (4-aminobutyl)-2,2-diphenylacetamide (0.032 g, 0.11 mmol) was added followed by HATU (0.057 g, 0.15 mmol) and DIPEA (0.02 g, 0.15 mmol). The whole mixture was stirred at 0° C. for 10 min and then was allowed warmed up to room temperature and stirred overnight. Resulting solution was washed with 20 ml water and 20 ml brine consecutively. The organic layer was later dried over anhydrous magnesium sulfate and concentrated under vacuum to give the crude compound. The crude compound was purified by column chromatography (0-20% ethyl acetate/hexane) to yield N-(4-(2,2-Diphenylacetamido)butyl)-2-(2-hydroxyphenyl)oxazole-4-carboxamide as an off-white amorphous solid (0.012 g, 26%). $^1$H NMR (δ, ppm, CDCl$_3$): 1.63 (m, 4H), 3.37 (t, 2H), 3.50 (t, 2H), 5.00 (s, 1H), 7.02 (t, 2H), 7.12 (t, 2H), 7.34 (m, 6H), 7.88 (dd, 2H), 8.28 (s, 1H), 10.17 (brs, 1H). $^{13}$C NMR (δ, ppm, CDCl$_3$): 27.13, 27.20, 38.80, 38.54, 96.26, 109.17, 119.98, 127.29, 128.79, 128.92, 134.59, 135.83, 139.36, 140.09, 152.61. UPLC: 6.492 min. ESI-MS m/z calculated: 470.208; found: 470.339 [M+H]+.

Example 11

N-(4-(3-(3,3-Diphenylpropyl)thioureido)butyl)-2-(2-hydroxyphenyl)oxazole-4-carboxamide

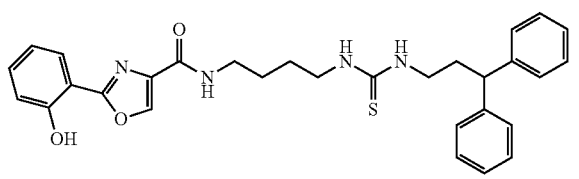 [SMILES: O=C(NCCCCNC(=S)NCCC(c1ccccc1)c1ccccc1)c1coc(-c2ccccc2O)n1]

The compound of this Example was made from compound 5 (0.006 g, 0.03 mmol), 1-(4-aminobutyl)-3-(3,3-diphenylpropyl)thiourea (0.01 g, 0.03 mmol) followed by HATU (0.019 g, 0.05 mmol) and DIPEA (0.007 g, 0.05 mmol) in 10 ml DCM using the procedure described in Example 10 in 75% yield as a pale yellow amorphous solid (0.012 g). $^1$H NMR ($\delta$, ppm, CDCl$_3$): 2.37-2.47 (m, 4H), 3.11-3.20 (m, 4H), 3.47 (q, 2H), 4.01 (dt, 2H), 5.88 (t, 1H), 6.729 (t, 1H), 7.02 (t, 1H), 7.12 (d, 1H), 7.18-7.19 (m, 4H), 7.20-7.32 (m, 6H), 7.44 (td, 1H), 7.88 (dd, 1H), 8.23 (s, 1H), 10.17 (brs, 1H). $^{13}$C NMR ($\delta$, ppm, CDCl$_3$): 35.11, 38.62, 39.71, 44.11, 46.88, 48.56, 49.26, 110.36, 117.35, 120.00, 126.52, 126.70, 127.73, 127.78 128.57, 128.79, 133.31, 135.81, 139.97, 143.39, 144.06, 144.35, 156.91, 159.68, 161.13, 161.46, 165.78. UPLC: 7.321 min. ESI-MS m/z calculated 529.228; found: 529.216 [M+H]+.

Example 12

N-(4-((3,3-Diphenylpropyl)amino)butyl)-2-(2-hydroxyphenyl)oxazole-4-carboxamide hydrochloride

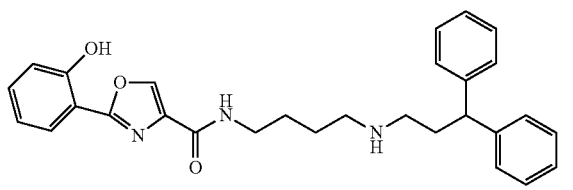 [SMILES: O=C(NCCCCNCCC(c1ccccc1)c1ccccc1)c1coc(-c2ccccc2O)n1]

The compound of Example 12 was made from compound 5 (0.037 g, 0.18 mmol), tert-butyl (4-aminobutyl)(3,3-diphenylpropyl)carbamate (0.07 g, 0.18 mmol), HATU (0.11 g, 0.3 mmol) and DIPEA (0.038 g, 0.3 mmol) in 4 ml DCM using the procedure described in Example 1. The reaction mixture was evaporated to dryness, and the crude N-Boc-protected intermediate compound was dissolved in 10 ml ethyl acetate without further purification. A 5.0 mL portion of HCl in acetic acid was added, and the mixture was stirred at room temperature overnight. The resulting mixture was extracted with water and the aqueous layer was lyophilized to afford final product N-(4-((3,3-Diphenylpropyl)amino) butyl)-2-(2-hydroxyphenyl)oxazole-4-carboxamide hydrochloride as a white amorphous solid (0.057 g, 63%). $^1$H NMR ($\delta$, ppm, CD$_3$OD): 1.58 (m, 2H), 2.41 (q, 2H), 2.75 (brs, 2H), 2.89 (brs, 2H), 3.28 (q, 2H), 3.49 (brs, 2H), 4.10 (t, 1H), 7.03 (t, 1H), 7.10 (d, 1H), 7.17-7.20 (m, 2H), 7.21-7.31 (m, 8H), 7.46 (t, 1H), 7.85 (dd, 1H), 8.74 (s, 1H), 8.90 (t, 1H), 9.02 (brs, 1H), 10.41 (s, 1H). $^{13}$C NMR ($\delta$, ppm, CD$_3$OD): 23.59, 26.80, 31.13, 38.86, 46.21, 46.71, 48.06, 111.05, 117.83, 120.29, 126.88, 127.31, 127.94, 129.07, 133.51, 136.50, 141.61, 144.34, 156.65, 159.82, 160.33. UPLC: 5.740 min. ESI-MS m/z calculated 470.245; found: 470.408 [M+H]+.

Example 13

Methyl 4-((2-(2-hydroxyphenyl)oxazole-4-carboxamido)methyl)benzoate

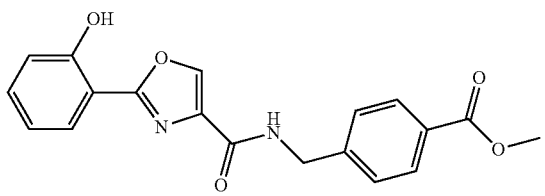 [SMILES: COC(=O)c1ccc(CNC(=O)c2coc(-c3ccccc3O)n2)cc1]

The compound of this Example was made from compound 5 (0.025 g, 0.12 mmol), methyl 4-(aminomethyl) benzoate hydrochloride (0.03 g, 0.15 mmol), HATU (0.076 g, 0.2 mmol) and DIPEA (0.033 g, 0.25 mmol) in 10 ml DCM using the procedure described in Example 1 in 40% yield as an off-white amorphous solid (0.017 g). $^1$H NMR ($\delta$, ppm, CDCl$_3$): 3.89 (s, 3H), 4.69 (d, 2H), 6.96 (t, 1H), 7.00 (d, 1H), 7.04 (brs, 1H), 7.37-7.42 (m, 3H), 7.84 (dd, 1H), 7.99 (d, 2H), 8.27 (s, 1H), 10.14 (s, 1H). ESI-MS m/z calculated: 353.114; found: 353.298 [M+H]+.

Example 14

4-((2-(2-Hydroxyphenyl)oxazole-4-carboxamido) methyl)benzoic acid

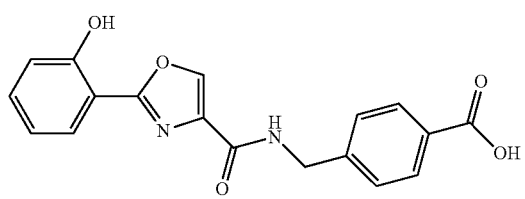 [SMILES: O=C(O)c1ccc(CNC(=O)c2coc(-c3ccccc3O)n2)cc1]

The compound of Example 14 was made from the compound of Example 13 (0.017 g, 0.05 mmol) and lithium hydroxide monohydrate (0.021 g, 0.5 mmol) in 10 ml/5 ml THF/H$_2$O using the procedure described for the synthesis of compound 5 in 83% yield as a pale yellow amorphous solid (0.014 g). $^1$H NMR ($\delta$, ppm, CD$_3$OD): 4.68 (s, 2H), 7.03 (t, 1H), 7.08 (d, 1H), 7.43 (t, 1H), 7.49 (d, 2H), 7.93 (dd, 1H), 8.02 (d, 2H), 8.51 (s, 1H).; m.p. 248-251° C.; ESI-MS m/z: calculated: 339.098; found: 339.294 [M+H]+.

Example 15

2-(2-Hydroxyphenyl)-N-(4-(phenylcarbamoyl)benzyl)oxazole-4-carboxamide

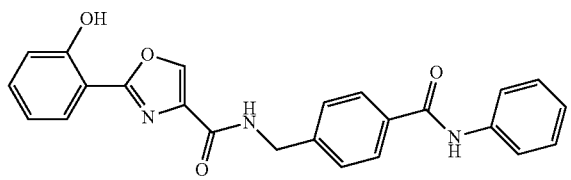 [SMILES: O=C(Nc1ccccc1)c1ccc(CNC(=O)c2coc(-c3ccccc3O)n2)cc1]

The compound of this Example was made from the compound of Example 14 (0.014 g, 0.04 mmol), aniline (0.005 g, 0.05 mmol), HATU (0.016 g, 0.05 mmol) and DIPEA (0.013 g, 0.1 mmol) in 3 ml DCM using the procedure described in Example 1 in 48% yield as a white amorphous solid (0.008 g). $^1$H NMR (δ, ppm, CH$_3$OD): 4.67 (s, 2H), 6.99 (t, 1H), 7.05 (d, 1H), 7.13 (t, 1H), 7.34 (m, 1H), 7.40 (s, 2H), 7.47 (d, 2H), 7.65 (d, 2H), 7.88 (m, 3H), 8.34 (s, 1H). $^{13}$C NMR (δ, ppm, CH$_3$OD): 42.73, 110.36, 117.18, 119.89, 120.92, 124.52, 126.62, 127.59, 127.72, 128.76, 133.17, 135.65, 138.16, 140.51, 161.19. UPLC: 6.094 min. ESI-MS m/z calculated: 414.146; found: 414.603 [M+H]$^+$.

Example 16

2-(2-Hydroxyphenyl)-N-(2-oxo-2-(phenylamino)ethyl)oxazole-4-carboxamide

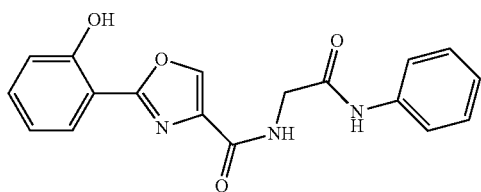 [SMILES: O=C(CNC(=O)c1coc(-c2ccccc2O)n1)Nc1ccccc1]

The compound of Example 16 was made from compound 5 (0.011 g, 0.05 mmol), 2-amino-N-phenylacetamide hydrochloride (0.01 g, 0.05 mmol), HATU (0.038 g, 0.1 mmol) and DIPEA (0.025 g, 0.2 mmol) in 3 ml DCM using the procedure described in Example 1 in 83% yield as a white amorphous solid (0.014 g). $^1$H NMR (δ, ppm, DMSO-d$_6$): 4.10 (d, 2H), 7.05 (q, 2H), 7.10 (d, 1H), 7.32 (t, 2H), 7.47 (d, 2H), 7.88 (d, 1H), 8.80 (s, 1H), 9.17 (t, 1H), 10.10 (s, 1H), 10.43 (s, 1H). $^{13}$C NMR (δ, ppm, DMSO-d$_6$): 46.87, 111.04, 117.84, 119.60, 120.34, 123.76, 127.36, 129.25, 133.56, 136.22, 139.37, 141.91, 156.69, 160.30, 160.41, 167.90. UPLC: 5.347 min. ESI-MS m/z calculated: 338.114; found 338.231 [M+H]$^+$.

Example 17

HDAC Inhibitory Assay Methods

The compounds of Examples 1-12 and 14-16 were evaluated for their ability to act as inhibitors of human HDAC. The compound of Example 13 was not tested. Recombinant human HDAC1, HDAC2, HDAC3/NcoR2, HDAC5, HDAC6, HDAC8, HDAC9, HDAC10 and HDAC11 were purchased from BPS Biosciences. Recombinant human HDAC4 and HDAC7 were purchased from Millipore. The substrate Boc-Lys(Ac)-AMC and Boc-Lys(Tfa)-AMC were purchased from Bachem. The substrate Ac-RHK(Ac)K(Ac)-AMC was purchased from Enzo Life Sciences. Due to the different specific activities of each isoform, different amount of enzyme was used in each isoform screening assay. In these assays, trichostatin A (TSA), suberanilohydroxamic acid and diphenylacetohydroxamic acid (DPAHA) were employed as positive controls. All determinations were carried out in triplicate, and reported values were the average of these determinations, which in no case varied by more than 5%.

For evaluating the inhibition of class I HDACs (HDAC1, HDAC2 and HDAC3) and class IIb HDACs (HDAC6 and HDAC10), 10 µl of test samples were first incubated with 20 ng HDAC1 (specific activity=500 pmol/min/µg), 20 ng HDAC2 (specific activity=675 pmol/min/µg), 5 ng HDAC3 (specific activity=2500 pmol/min/µg), 25 ng HDAC6 (specific activity=215 pmol/min/µg) and 250 ng HDAC10 (specific activity=2.3 pmol/min/µg) respectively. Then 25 µl of the Boc-Lys(Ac)-AMC substrate (50 µM final concentration) was added and incubated at 37° C. for 30-60 min, and followed by adding 50 µl of developer (1 mg/ml trypsin and 1 µM TSA). The last step was reading the samples in a SpectraMax M5 plate reader (Molecular Devices) at an excitation wavelength of 360 nm and an emission wavelength of 460 nm.

For evaluating the inhibition of class IIa HDACs (HDAC4, HDAC5, HDAC7 and HDAC9) and class IV HDAC (HDAC11), 10 µl of test samples were first incubated with 1 ng HDAC4 (specific activity=15400 pmol/min/µg), 5 ng HDAC5 (specific activity=2521 pmol/min/µg), 1 ng HDAC7 (specific activity=26340 pmol/min/µg), 5 ng HDAC9 (specific activity=3000 pmol/min/µg), and 500 ng HDAC11 (specific activity=1.8 pmol/min/µg) respectively. Then 25 µl of the Boc-Lys(Tfa)-AMC substrate (50 µM final concentration) was added and incubated at 37° C. for 30-60 min, and followed by adding 50 µl of developer. The last step was to read the samples in a SpectraMax M5 plate reader (Molecular Devices) at an excitation wavelength of 360 nm and an emission wavelength of 460 nm.

For evaluating the inhibition of HDAC8, 10 µl of test samples were first incubated with 25 ng HDAC8 (specific activity 298 pmol/min/µg). Then 25 µl of the fluorogenic peptide from p53 residues 379-382 (Ac-RHK(Ac)K(Ac)-AMC, 50 µM final concentration) was added and incubated at 37° C. for 30-60 min, and followed by adding 50 µl of developer (1 mg/ml trypsin and 1 uM TSA). The last step was to read the samples in a SpectraMax M5 plate reader (Molecular Devices) at an excitation wavelength of 360 nm and an emission wavelength of 460 nm.

Table 1 below shows the inhibitory activity of representative compounds of the invention:

TABLE 1

| Ex. No. | HDAC 1 | HDAC 2 | HDAC 3 | HDAC 4 | HDAC 5 | HDAC 6 | HDAC 7 | HDAC 8 | HDAC 9 | HDAC 10 | HDAC 11 |
|---|---|---|---|---|---|---|---|---|---|---|---|
| 1 | 62.5% | 29.5% | 22.5% | 17.1% | 9.3% | 50.3% | 1.3% | 0 | 20.5% | 48.8% | 21.8% |
| 2 | 68.0% | 54.1% | 37.8% | 20.7% | 14.9% | 61.6% | 9.2% | 23.3% | 33.3% | 47.1% | 23.1% |
| 3 | 43.9% | 34.8% | 23.7% | 8.5% | 0 | 49.1% | 4.1% | 16.7% | 21.6% | 35.7% | 39.5% |
| 4 | 35.9% | 28.7% | 37.5% | 25.8% | 11.3% | 48.1% | 0.7% | 7.2% | 28.2% | 69.8% | 45.2% |
| 5 | 62.2% | 31.9% | 30.2% | 25.5% | 0 | 45.6% | 19.4% | 7.2% | 32.4% | 58.6% | 28.4% |
| 6 | 61.4% | 52.2% | 40.1% | 24.4% | 9.2% | 47.8% | 1.4% | 17.9% | 20.8% | 48.7% | 47.8% |
| 7 | 47.8% | 45.2% | 32.3% | 21.3% | 3.2% | 40.4% | 3.8% | 10.6% | 15.5% | 44.5% | 49.9% |
| 8 | 41.7% | 36.0% | 18.9% | 7.5% | 0 | 30.8% | 3.8% | 7.7% | 18.4% | 44.8% | 26.0% |
| 9 | 35.2% | 25.4% | 11.0% | 17.5% | 10.3% | 46.0% | 1.1% | 9.6% | 16.4% | 32.1% | 33.8% |
| 10 | 27.2% | 0 | 4.0% | 4.8% | 1.4% | 26.7% | 2.2% | 0 | 9.0% | 56.5% | 30.1% |
| 11 | 43.3% | 1.3% | 3.7% | 55.8% | 43.5% | 50.2% | 21.9% | 0 | 70.2% | 91.2% | 69.9% |
| 12 | 32.2% | 19.7% | 18.1% | 6.5% | 6.9% | 28.9% | 0 | 14.0% | 16.4% | 26.2% | 39.1% |
| 14 | 70.1% | 56.5% | 39.7% | 24.2% | 12.6% | 60.3% | 9.3% | 20.0% | 26.3% | 47.2% | 49.2% |
| 15 | 47% | 41.3% | 15.8% | 18.3% | 0 | 30.8% | 9.9% | 0 | 24.3% | 56.3% | 20.1% |
| 16 | 25.5% | 32.0% | 36.9% | 28.1% | 12.5% | 59.9% | 0 | 15.0% | 14.2% | 54.7% | 46.6% |

Example 18

Cell Proliferation Assay

The cytotoxicity of representative compounds of the invention was determined by MTS assay, following the protocol of CellTiter 96® AQueous Non-Radioactive Cell Proliferation Assay (Promega). The cells used in this assay were MV4-11 (human, macrophage, biphenotypic B myelomonocytic leukemia) and MCF-7 (human, epithelial, adenocarcinoma). 10000 cells/well in 99 µl medium were seeded in a 96-well plate and were treated with 1 µl test compounds in DMSO with gradually increased concentrations (final concentration from 1 µM to 100 µM). The MV-4-11 cells were incubated with the representative compounds for 24 hours at 37° C. in 5% $CO_2$ while the MCF-7 cells were first seeded on the 96-well plate and were allowed to attach for 1 day and then were incubated with different concentrations of the representative compound for 72 hours at 37° C. in 5% $CO_2$. After 24 or 72 hours 20 µl of MTS reagent solution was added into each well and the cells were incubated for another 4 hours at 37° C. under 5% $CO_2$ environment. The absorbance was measured at 490 nm in a SpectraMax M5 plate reader (Molecular Devices) to determine the cell viability. The absorbance was directly proportional to the amount of viable cells. All determinations were carried out in triplicate, and reported values in Table 2 below were the average of these determinations, which in no case varied by more than 5%.

TABLE 2

| Example No. | $IC_{50}$ (µM) |
|---|---|
| 1 | 25 |
| 2 | 7.6 |
| 3 | 40 |
| 6 | >100 |

REFERENCES

1. P. A. Marks, T. Miller and V. M. Richon, *Curr. Opin. Pharmacol.*, 2003, 3, 344.
2. J. E. Bolden, M. J. Peart and R. W. Johnstone, *Nat. Rev. Drug Disc.*, 2006, 5, 769.
3. R. W. Johnstone, *Nat. Rev. Drug Disc.*, 2002, 1, 287.
4. M. S. Finnin, J. R. Donigian, A. Cohen, V. M. Richon, R. A. Rifkind, P. A. Marks, R. Breslow and N. P. Pavletich, *Nature*, 1999, 401, 188.
5. R. R. Frey, C. K. Wada, R. B. Garland, M. L. Curtin, M. R. Michaelides, J. Li, L. J. Pease, K. B. Glaser, P. A. Marcotte, J. J. Bouska, S. S. Murphy and S. K. Davidsen, *Bioorg. Med. Chem. Lett.*, 2002, 12, 3443.
6. L. A. Reiter, R. P. Robinson, K. F. McClure, C. S. Jones, M. R. Reese, P. G. Mitchell, I. G. Otterness, M. L. Bliven, J. Liras, S. R. Cortina, K. M. Donahue, J. D. Eskra, R. J. Griffiths, M. E. Lame, A. Lopez-Anaya, G. J. Martinelli, S. M. McGahee, S. A. Yocum, L. L. Lopresti-Morrow, L. M. Tobiassen and M. L. Vaughn-Bowser, *Bioorg. Med. Chem. Lett.*, 2004, 14, 3389.
7. E. Farkas, Y. Katz, S. Bhusare, R. Reich, G. V. Roschenthaler, M. Konigsmann and E. Breuer, *Journal of biological inorganic chemistry: JBIC: a publication of the Society of Biological Inorganic Chemistry*, 2004, 9, 307.
8. E. C. O'Brien, E. Farkas, M. J. Gil, D. Fitzgerald, A. Castineras and K. B. Nolan, *Journal of inorganic biochemistry*, 2000, 79, 47.
9. T. Suzuki and N. Miyata, *Current medicinal chemistry*, 2005, 12, 2867.
10. T. H. Graham, *Org. Lett.*, 2010, 12, 3614.
11. B. D. Strahl and C. D. Allis, *Nature*, 2000, 403, 41.
12. J. C. Hansen, C. Tse and A. P. Wolffe, *Biochemistry*, 1998, 37, 17637.
13. S. Varghese, D. Gupta, T. Baran, A. Jiemjit, S. D. Gore, R. A. Casero, Jr. and P. M. Woster, *J. Med. Chem.*, 2005, 48, 6350.
14. S. Varghese, T. Senanayake, T. Murray-Stewart, K. Doering, A. Fraser, R. A. Casero and P. M. Woster, *J. Med. Chem.*, 2008, 51, 2447.
15. T. Abbas and A. Dutta, *Nature reviews. Cancer*, 2009, 9, 400.
16. R. B. Gartenhaus, P. Wang and P. Hoffmann, *Proc. Nat'l. Acad. Sci. U.S.A.*, 1996, 93, 265.
17. V. M. Richon, T. W. Sandhoff, R. A. Rifkind and P. A. Marks, *Proc. Nat'l. Acad. Sci. U.S.A.*, 2000, 97, 10014.
18. P. Chandran, A. Kavalakatt, G. L. Malarvizhi, D. R. Vasanthakumari, A. P. Retnakumari, N. Sidharthan, K. Pavithran, S. Nair and M. Koyakutty, *Nanomedicine: nanotechnology, biology, and medicine*, 2014, 10, 721.
19. K. Huber, G. Doyon, J. Plaks, E. Fyne, J. W. Mellors and N. Sluis-Cremer, *J. Biol. Chem.*, 2011, 286, 22211.

20. R. D. Kelly and S. M. Cowley, *Biochem. Soc. Trans.*, 2013, 41, 741.
21. C. A. Lipinski, F. Lombardo, B. W. Dominy and P. J. Feeney, *Adv. Drug Deliv. Rev.*, 2001, 46, 3.
22. B. E. Lauffer, R. Mintzer, R. Fong, S. Mukund, C. Tam, I. Zilberleyb, B. Flicke, A. Ritscher, G. Fedorowicz, R. Vallero, D. F. Ortwine, J. Gunzner, Z. Modrusan, L. Neumann, C. M. Koth, P. J. Lupardus, J. S. Kaminker, C. E. Heise and P. Steiner, *J. Biol. Chem.*, 2013, 288, 26926.

It is to be understood that the invention is not limited to the particular embodiments of the invention described above, as variations of the particular embodiments may be made and still fall within the scope of the appended claims.

What is claimed is:

1. A compound according to formula (I):

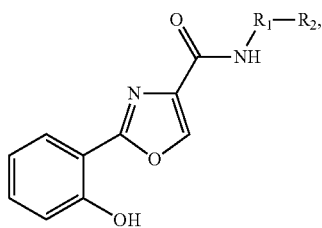

(I)

wherein:
R$_1$ is a bond or lower alkyl; and
R$_2$ is -phenyl, optionally substituted independently with
—C(O)NH-phenyl, —C(O)OCH$_3$, phenyl or —C(O)OH,
—CH(phenyl)$_2$,
-naphthalenyl,
-1H-indolyl,
-dioxoisoindolinyl,
—NHC(O)CH(phenyl)$_2$,
—NHC(S)NHCH$_2$CH$_2$CH(phenyl)$_2$,
—NHCH$_2$CH$_2$CH(phenyl)$_2$ or
—C(O)NH-phenyl,
or a pharmaceutically acceptable salt thereof.

2. The compound according to claim 1, wherein R$_1$ is a bond.

3. The compound according to claim 1, wherein R$_1$ is lower alkyl.

4. The compound according to claim 1, wherein R$_2$ is phenyl.

5. The compound according to claim 1, wherein R$_2$ is phenyl substituted independently with —C(O)NH-phenyl, —C(O)OCH$_3$, —C(O)OH or phenyl.

6. The compound according to claim 1, wherein R$_2$ is —CH(phenyl)$_2$.

7. The compound according to claim 1, wherein R$_2$ is naphthalenyl, 1H-indolyl or dioxoisoindolinyl.

8. The compound according to claim 1, wherein R$_2$ is —NHC(O)CH(phenyl)$_2$, —NHC(S)NHCH$_2$CH$_2$CH(phenyl)$_2$, —NHCH$_2$CH$_2$CH(phenyl)$_2$ or —C(O)NH-phenyl.

9. The compound according to claim 1, wherein R$_1$ is a bond and R$_2$ is phenyl, optionally substituted independently with —C(O)NH-phenyl, —C(O)OCH$_3$, —C(O)OH or phenyl.

10. The compound according to claim 1, wherein R$_1$ is a bond and R$_2$ is —CH(phenyl)$_2$.

11. The compound according to claim 1, wherein R$_1$ is lower alkyl and R$_2$ is —CH(phenyl)$_2$, -naphthalenyl, -1H-indolyl, -dioxoisoindolinyl, —NHC(O)CH(phenyl)$_2$, —NHC(S)NHCH$_2$CH$_2$CH(phenyl)$_2$, —NHCH$_2$CH$_2$CH(phenyl)$_2$ or —C(O)NH-phenyl.

12. The compound according to claim 1, wherein said lower alkyl is methyl, ethyl, propyl or butyl.

13. The compound according to claim 1, wherein said lower alkyl is methyl or ethyl.

14. The compound according to claim 1, wherein said lower alkyl is methyl.

15. The compound according to claim 1, wherein said compound is:
2-(2-Hydroxyphenyl)-N-phenyloxazole-4-carboxamide;
N-Benzhydryl-2-(2-hydroxyphenyl)oxazole-4-carboxamide;
N-(2,2-Diphenylethyl)-2-(2-hydroxyphenyl)oxazole-4-carboxamide;
N-(3,3-Diphenylpropyl)-2-(2-hydroxyphenyl)oxazole-4-carboxamide;
N-([1,1'-Biphenyl]-4-yl)-2-(2-hydroxyphenyl)oxazole-4-carboxamide;
N-([1,1'-Biphenyl]-4-ylmethyl)-2-(2-hydroxyphenyl)oxazole-4-carboxamide;
2-(2-Hydroxyphenyl)-N-(naphthalen-1-ylmethyl)oxazole-4-carboxamide;
N-(2-(1H-Indol-3-yl)ethyl)-2-(2-hydroxyphenyl)oxazole-4-carboxamide;
N-(4-(1,3-Dioxoisoindolin-2-yl)butyl)-2-(2-hydroxyphenyl)oxazole-4-carboxamide;
N-(4-(2,2-Diphenylacetamido)butyl)-2-(2-hydroxyphenyl)oxazole-4-carboxamide;
N-(4-(3-(3,3-Diphenylpropyl)thioureido)butyl)-2-(2-hydroxyphenyl)oxazole-4-carboxamide;
N-(4-((3,3-Diphenylpropyl)amino)butyl)-2-(2-hydroxyphenyl)oxazole-4-carboxamide hydrochloride;
Methyl 4-((2-(2-hydroxyphenyl)oxazole-4-carboxamido)methyl)benzoate;
4-((2-(2-Hydroxyphenyl)oxazole-4-carboxamido)methyl)benzoic acid;
2-(2-Hydroxyphenyl)-N-(4-(phenylcarbamoyl)benzyl)oxazole-4-carboxamide; or
2-(2-Hydroxyphenyl)-N-(2-oxo-2-(phenylamino)ethyl)oxazole-4-carboxamide.

16. A pharmaceutical composition, comprising a therapeutically effective amount of a compound according to claim 1 or a pharmaceutically acceptable salt thereof and a pharmaceutically acceptable carrier.

* * * * *